US008431671B2

(12) United States Patent
Sherman et al.

(10) Patent No.: US 8,431,671 B2
(45) Date of Patent: *Apr. 30, 2013

(54) STRUCTURED POLYDIORGANOSILOXANE POLYAMIDE CONTAINING DEVICES AND METHODS

(75) Inventors: Audrey A. Sherman, St. Paul, MN (US); Mark R. Richmond, Austin, TX (US); Raymond P. Johnston, Lake Elmo, MN (US); Mieczyslaw H. Mazurek, Roseville, MN (US); John C. Hulteen, Afton, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1123 days.

This patent is subject to a terminal disclaimer.

(21) Appl. No.: 12/055,386

(22) Filed: Mar. 26, 2008

(65) Prior Publication Data
US 2009/0242048 A1    Oct. 1, 2009

(51) Int. Cl.
C08G 77/26    (2006.01)
C08G 77/04    (2006.01)
C08L 77/00    (2006.01)
C08L 83/00    (2006.01)
F15C 1/06    (2006.01)
H01B 7/42    (2006.01)

(52) U.S. Cl.
USPC ............... 528/38; 528/26; 528/28; 525/431; 137/833; 174/16.1

(58) Field of Classification Search ............ 137/833; 165/80.4; 361/699, 702; 174/16.1, 16.3; 257/714; 528/26, 28, 38; 525/431
See application file for complete search history.

(56) References Cited

U.S. PATENT DOCUMENTS

| 2,532,011 | A |   | 11/1950 | Dahlquist et al. |
| 2,676,182 | A |   | 4/1954  | Daudt et al. |
| 3,392,143 | A | * | 7/1968  | Holub .................... 528/26 |
| 3,627,851 | A |   | 12/1971 | Brady |
| 3,772,247 | A |   | 11/1973 | Flanningan |
| 3,890,269 | A |   | 6/1975  | Martin |
| 4,119,615 | A |   | 10/1978 | Schulze |
| 4,450,472 | A | * | 5/1984  | Tuckerman et al. ........ 257/713 |
| 4,661,577 | A |   | 4/1987  | Jo Lane et al. |
| 4,822,852 | A | * | 4/1989  | Wittmann et al. .......... 525/66 |
| 4,889,753 | A |   | 12/1989 | Brown et al. |
| 4,935,484 | A |   | 6/1990  | Wolfgruber et al. |
| 5,003,429 | A | * | 3/1991  | Baker et al. ................ 361/704 |

(Continued)

FOREIGN PATENT DOCUMENTS

| EP | 0378420 | 7/1990 |
| EP | 0433070 | 6/1991 |

(Continued)

OTHER PUBLICATIONS

U.S. Appl. No. 11/821,568, filed Jun. 22, 2007, Sherman et al.

(Continued)

Primary Examiner — Craig Schneider
Assistant Examiner — Jonathan Waddy
(74) Attorney, Agent, or Firm — Jeffrey M. Olofson

(57) ABSTRACT

Devices including a polydiorganosiloxane polyamide containing material having a microstructured surface are disclosed herein. Such devices can optionally include a flex circuit attached to the microstructured surface and can be useful, for example, in fluid handling applications.

25 Claims, 2 Drawing Sheets

U.S. PATENT DOCUMENTS

| | | | |
|---|---|---|---|
| 5,026,890 A | 6/1991 | Webb et al. | |
| 5,082,706 A | 1/1992 | Tangney | |
| 5,091,483 A | 2/1992 | Mazurek et al. | |
| 5,110,890 A | 5/1992 | Butler | |
| 5,214,119 A | 5/1993 | Leir et al. | |
| 5,248,739 A | 9/1993 | Schmidt et al. | |
| 5,276,122 A | 1/1994 | Aoki et al. | |
| 5,290,615 A | 3/1994 | Tushaus et al. | |
| 5,302,685 A | 4/1994 | Tsumura et al. | |
| 5,319,040 A | 6/1994 | Wengrovius et al. | |
| 5,461,134 A | 10/1995 | Leir et al. | |
| 5,512,650 A | 4/1996 | Leir et al. | |
| 5,514,120 A | 5/1996 | Johnson et al. | |
| 5,539,033 A | 7/1996 | Bredahl et al. | |
| 5,663,262 A | 9/1997 | Shirakawa et al. | |
| 5,981,680 A | 11/1999 | Petroff et al. | |
| 6,051,216 A | 4/2000 | Barr et al. | |
| 6,123,890 A | 9/2000 | Mazurek et al. | |
| 6,315,851 B1 | 11/2001 | Mazurek et al. | |
| 6,355,759 B1 | 3/2002 | Sherman et al. | |
| 6,375,871 B1 * | 4/2002 | Bentsen et al. | 264/1.6 |
| 6,407,195 B2 | 6/2002 | Sherman et al. | |
| 6,420,622 B1 | 7/2002 | Johnston et al. | |
| 6,440,880 B2 | 8/2002 | Mazurek et al. | |
| 6,441,118 B2 | 8/2002 | Sherman et al. | |
| 6,531,620 B2 | 3/2003 | Brader et al. | |
| 6,534,615 B2 | 3/2003 | Schafer et al. | |
| 6,664,359 B1 | 12/2003 | Kangas et al. | |
| 6,730,397 B2 | 5/2004 | Melancon et al. | |
| 6,803,090 B2 | 10/2004 | Castiglione et al. | |
| 6,838,150 B2 | 1/2005 | Mazurek et al. | |
| 6,846,893 B1 | 1/2005 | Sherman et al. | |
| 7,012,110 B2 | 3/2006 | Sherman et al. | |
| 7,026,424 B2 | 4/2006 | Schafer et al. | |
| 7,090,922 B2 | 8/2006 | Zhou et al. | |
| 7,105,809 B2 | 9/2006 | Wood et al. | |
| 7,153,924 B2 | 12/2006 | Kuepfer et al. | |
| 7,250,210 B2 | 7/2007 | Mazurek et al. | |
| 7,371,464 B2 * | 5/2008 | Sherman et al. | 428/447 |
| 7,947,376 B2 * | 5/2011 | Sherman et al. | 428/447 |
| 2003/0235553 A1 | 12/2003 | Lu et al. | |
| 2004/0115153 A1 | 6/2004 | Yu | |
| 2004/0120912 A1 | 6/2004 | Yu | |
| 2004/0262223 A1 * | 12/2004 | Strook et al. | 210/634 |
| 2005/0136266 A1 | 6/2005 | Zhou et al. | |
| 2005/0282024 A1 | 12/2005 | Sherman et al. | |
| 2007/0148474 A1 | 6/2007 | Leir et al. | |
| 2007/0148475 A1 | 6/2007 | Sherman et al. | |
| 2007/0149745 A1 | 6/2007 | Leir et al. | |
| 2007/0177272 A1 | 8/2007 | Benson et al. | |
| 2007/0177273 A1 | 8/2007 | Benson et al. | |
| 2011/0189421 A1 * | 8/2011 | Sherman et al. | 428/36.91 |

FOREIGN PATENT DOCUMENTS

| | | | |
|---|---|---|---|
| EP | 0311262 | | 12/1992 |
| GB | 1348783 | * | 3/1974 |
| JP | HEI 2-36234 | | 2/1990 |
| WO | WO97/40103 | | 10/1997 |
| WO | WO2004/054523 | | 7/2004 |

OTHER PUBLICATIONS

U.S. Appl. No. 11/821,571, filed Jun. 22, 2007, Leir et al.
U.S. Appl. No. 11/821,572, filed Jun. 22, 2007, Sherman et al.
U.S. Appl. No. 11/821,575, filed Jun. 22, 2007, Sherman et al.
U.S. Appl. No. 11/821,596, filed Jun. 22, 2007, Sherman et al.
McGrath et al., "Synthesis and Characterization of Segmented Siloxane Copolymers", Polymer Preprints, vol. 39, No. 1, 1998, pp. 455-456.
*Encyclopedia of Polymer Science and Engineering*, vol. 15, John Wiley & Sons, New York, (1989), pp. 265-270.
ASTM-D 1003-95, "Standard Test Method for Haze and Luminous Transmittance of Transparent Plastics," *Annual Book of ASTM Standards*, pp. 197-201 (1995).
Smith, *Modern Optical Engineering*, McGraw-Hill Book Company, New York, NY 1966, pp. 104-105.

* cited by examiner

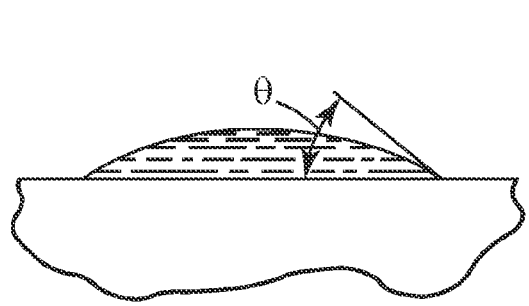
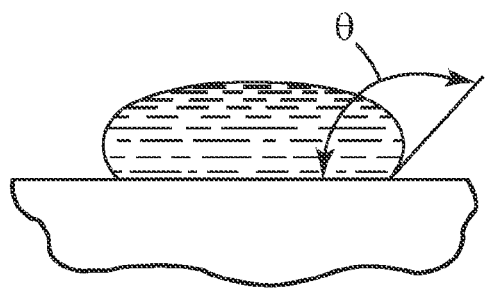
*Fig. 1a*  *Fig. 1b*
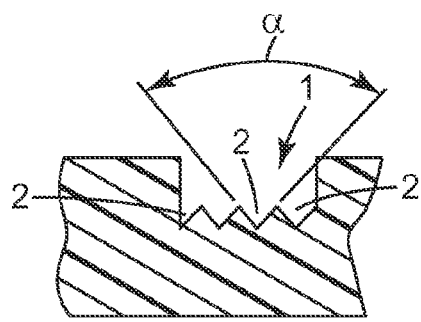
*Fig. 2*
*Fig. 3*
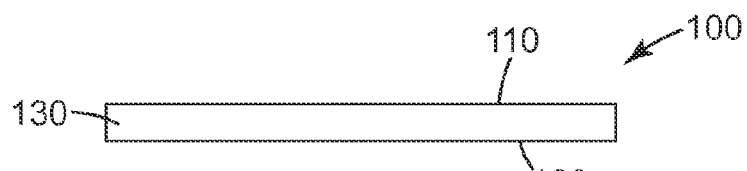
*Fig. 4*
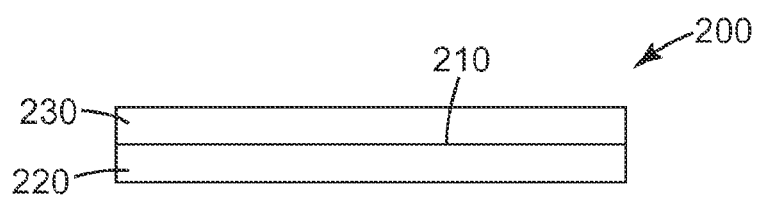
*Fig. 5*

STRUCTURED POLYDIORGANOSILOXANE POLYAMIDE CONTAINING DEVICES AND METHODS

BACKGROUND

Fluid handling capabilities can be required in devices that can be used in a wide variety of applications. For example, a device may require fluid handling capabilities for collecting a fluid for subsequent analysis, for transporting a fluid to storage, for liquid processing, or combinations thereof. Depending on the specific application, there may be a need for devices that can handle a wide range of fluids having varying properties. For example, a wide variety of devices having the capability of collecting, handling, and/or transporting various biological fluids can be used, for example, in medical treatments and diagnostic procedures.

To meet the need for devices with fluid handling capabilities, there is a need for new materials that can be incorporated into devices to influence the fluid handling capabilities of such devices. Further, there is a desire for new methods of making such fluid handling devices that can, for example, simplify the manufacturing of such devices.

SUMMARY

In one aspect, the present disclosure provides a device (e.g., a fluid handling device) including a polydiorganosiloxane polyamide containing material having a microstructured surface that can include, for example, one or more channels and/or wells. In some embodiments, the device further includes a flex circuit attached to the microstructured surface. For embodiments in which the device is a fluid handling device, the device can be a capillary device. The microstructured surface can be hydrophobic or hydrophilic, and is typically hydrophilic when used for handling aqueous fluids.

In another aspect, the present disclosure provides a fluid handling device that includes: a flex circuit; and a structured material (e.g., a microstructured material) attached to the flex circuit, wherein the structured material includes one or more polydiorganosiloxane polyamides. In certain embodiments, the structured material is adhered directly to at least a portion of the flex circuit, sometimes without additional adhesive. The flex circuit can include, for example, a polyester substrate such as a polyethylene terephthalate (PET) substrate. The fluid handling device can optionally include a source of potential.

In another aspect, the present disclosure provides a method of making a fluid handling device. In one embodiment, the method includes: providing a structured material including one or more polydiorganosiloxane polyamides; and attaching the structured material to a flex circuit, oftentimes a film-based flex circuit. The flex circuit can include, for example, a polyester substrate such as a polyethylene terephthalate substrate. The structured material can be attached to the flex circuit, for example, by heating and/or applying pressure to the structured material. In certain embodiments, the structured material can advantageously be attached to the flex circuit without the use of an additional adhesive. In other certain embodiments, the device can advantageously be prepared without the use of lithographic methods (e.g., photolithographic methods) and/or any other wet chemical processes.

In still another aspect, the present disclosure provides a method of making a fluid handling device. The method includes: forming a microstructured surface on a surface of a polymeric material including one or more polydiorganosiloxane polyamides; and attaching the microstructured surface to a flex circuit.

As used herein, "a," "an," "the," and "at least one" are used interchangeably and mean one or more than one.

As used herein, the term "comprising," which is synonymous with "including" or "containing," is inclusive, open-ended, and does not exclude additional unrecited elements or method steps.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the term "or" is generally employed in its sense including "and/or" unless the content clearly dictates otherwise.

The term "and/or" means one or all of the listed elements or a combination of any two or more of the listed elements.

The term "alkenyl" refers to a monovalent group that is a radical of an alkene, which is a hydrocarbon with at least one carbon-carbon double bond. The alkenyl can be linear, branched, cyclic, or combinations thereof and typically contains 2 to 20 carbon atoms. In some embodiments, the alkenyl contains 2 to 18, 2 to 12, 2 to 10, 4 to 10, 4 to 8, 2 to 8, 2 to 6, or 2 to 4 carbon atoms. Exemplary alkenyl groups include ethenyl, n-propenyl, and n-butenyl.

The term "alkyl" refers to a monovalent group that is a radical of an alkane, which is a saturated hydrocarbon. The alkyl can be linear, branched, cyclic, or combinations thereof and typically has 1 to 20 carbon atoms. In some embodiments, the alkyl group contains 1 to 18, 1 to 12, 1 to 10, 1 to 8, 1 to 6, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combinations thereof. The alkylene often has 1 to 20 carbon atoms. In some embodiments, the alkylene contains 1 to 18, 1 to 12, 1 to 10, 1 to 8, 1 to 6, or 1 to 4 carbon atoms. The radical centers of the alkylene can be on the same carbon atom (i.e., an alkylidene) or on different carbon atoms.

The term "alkoxy" refers to a monovalent group of formula —OR where R is an alkyl group.

The term "alkoxycarbonyl" refers to a monovalent group of formula —(CO)OR where R is an alkyl group and (CO) denotes a carbonyl group with the carbon attached to the oxygen with a double bond.

The term "aralkyl" refers to a monovalent group of formula —$R^a$—Ar where $R^a$ is an alkylene and Ar is an aryl group. That is, the aralkyl is an alkyl substituted with an aryl.

The term "aralkylene" refers to a divalent group of formula —$R^a$—$Ar^a$— where $R^a$ is an alkylene and $Ar^a$ is an arylene (i.e., an alkylene is bonded to an arylene).

The term "aryl" refers to a monovalent group that is aromatic and carbocyclic. The aryl can have one to five rings that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "arylene" refers to a divalent group that is carbocyclic and aromatic. The group has one to five rings that are connected, fused, or combinations thereof. The other rings can be aromatic, non-aromatic, or combinations thereof. In some embodiments, the arylene group has up to 5 rings, up to 4 rings, up to 3 rings, up to 2 rings, or one aromatic ring. For example, the arylene group can be phenylene.

The term "aryloxy" refers to a monovalent group of formula —OAr where Ar is an aryl group.

The term "carbonyl" refers to a divalent group of formula —(CO)— where the carbon atom is attached to the oxygen atom with a double bond.

The term "halo" refers to fluoro, chloro, bromo, or iodo.

The term "haloalkyl" refers to an alkyl having at least one hydrogen atom replaced with a halo. Some haloalkyl groups are fluoroalkyl groups, chloroalkyl groups, or bromoalkyl groups.

The term "heteroalkylene" refers to a divalent group that includes at least two alkylene groups connected by a thio, oxy, or —NR— where R is alkyl. The heteroalkylene can be linear, branched, cyclic, or combinations thereof and can include up to 60 carbon atoms and up to 15 heteroatoms. In some embodiments, the heteroalkylene includes up to 50 carbon atoms, up to 40 carbon atoms, up to 30 carbon atoms, up to 20 carbon atoms, or up to 10 carbon atoms. Some heteroalkylenes are polyalkylene oxides where the heteroatom is oxygen.

The term "oxalyl" refers to a divalent group of formula —(CO)—(CO)— where each (CO) denotes a carbonyl group.

The terms "oxalylamino" and "aminoxalyl" are used interchangeably to refer to a divalent group of formula —(CO)—(CO)—NH— where each (CO) denotes a carbonyl.

The term "aminoxalylamino" refers to a divalent group of formula —NH—(CO)—(CO)—NRd- where each (CO) denotes a carbonyl group and Rd is hydrogen, alkyl, or part of a heterocyclic group along with the nitrogen to which they are both attached. In most embodiments, Rd is hydrogen or alkyl. In many embodiments, Rd is hydrogen.

The term "polyvalent" refers to a group having a valence of greater than 2.

The terms "polymer" and "polymeric material" refer to both materials prepared from one monomer such as a homopolymer or to materials prepared from two or more monomers such as a copolymer, terpolymer, or the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The term "polydiorganosiloxane" refers to a divalent segment of formula

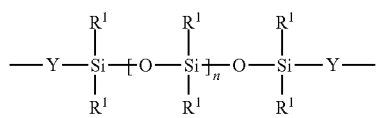

where each $R^1$ is independently an alkyl, haloalkyl, aralkyl, alkenyl, aryl, or aryl substituted with an alkyl, alkoxy, or halo; each Y is independently an alkylene, aralkylene, or a combination thereof, and subscript n is independently an integer of 0 to 1500.

The terms "room temperature" and "ambient temperature" are used interchangeably to mean temperatures in the range of 20° C. to 25° C.

The above summary of the present invention is not intended to describe each disclosed embodiment or every implementation of the present invention. The description that follows more particularly exemplifies illustrative embodiments. In several places throughout the application, guidance is provided through lists of examples, which can be used in various combinations. In each instance, the recited list serves only as a representative group and should not be interpreted as an exclusive list.

BRIEF DESCRIPTION OF THE DRAWING

FIGS. 1a and 1b are schematic diagrams used to illustrate interaction of a liquid on a surface.

FIG. 2 is a cross-sectional cutaway view of an illustrative embodiment of a structured surface having channels within channels.

FIG. 3 is a schematic diagram of a device that includes a polydiorganosiloxane polyamide containing material.

FIG. 4 is a schematic diagram of a device that includes a layer of a polydiorganosiloxane polyamide containing material.

FIG. 5 is a schematic diagram of a fluid handling device that includes a polydiorganosiloxane polyamide containing material and a substrate.

Figure 6:
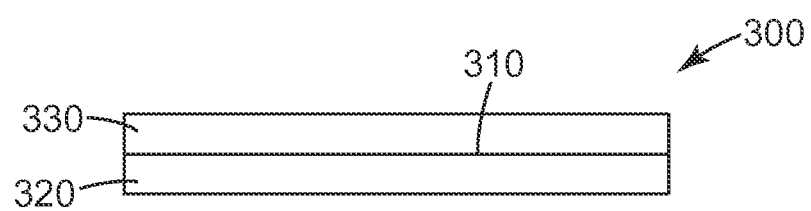
FIG. 6 is a schematic diagram of a fluid handling device that includes a polydiorganosiloxane polyamide containing material and a flexible circuit.

The above brief description of drawings illustrating various embodiments of the present invention is not intended to describe each embodiment or every implementation of the present invention. Rather, a more complete understanding of the invention will become apparent and appreciated by reference to the following description and claims in view of the accompanying drawings. Further, it is to be understood that other embodiments may be utilized and structural changes may be made without departing from the scope of the present invention.

DETAILED DESCRIPTION OF ILLUSTRATIVE EMBODIMENTS

The present disclosure relates to devices that include a polydiorganosiloxane polyamide containing material. Such devices can be used in many applications. In some embodiments, a polydiorganosiloxane polyamide containing material can be used in devices, e.g., devices that can control or transport fluids. In some embodiments, devices include a polydiorganosiloxane polyamide containing material having a structured surface that can control or transport fluids.

As used herein, a "structured material" refers to a material that includes at least one surface having features that may or may not be microscopic. As used herein, a "microstructured material" refers to a material that includes at least one surface having one or more microscopic features.

As used herein, a "microstructured" surface means that the surface has a configuration of features in which at least 2 dimensions of the features are microscopic. As used herein, the term "microscopic" refers to features of small enough dimension so as to require an optic aid to the naked eye when viewed from a plane of view to determine its shape. One criterion is found in *Modern Optical Engineering* by W. J. Smith, McGraw-Hill, 1966, pages 104-105 whereby visual acuity "is defined and measured in terms of the angular size of the smallest character that can be recognized." Normal visual acuity is considered to be when the smallest recognizable letter subtends an angular height of 5 minutes of arc on the retina. At a typical working distance of 250 mm (10 inches), this yields a lateral dimension of 0.36 mm (0.0145 inch) for this object.

A microstructured surface can include few or many microscopic features (e.g., tens, hundreds, thousands, or more). The microscopic features can all be the same, or one or more can be different. The microscopic features can all have the same dimensions, or one or more can have different dimensions. For example, a microstructured surface can include features that are precisely replicated from a predetermined pattern and can form, for example, a series of individual open capillary channels that extend along a major surface. These microreplicated channels formed in sheets, films, or tubes can be uniform and regular along substantially each channel length and can be uniform from channel to channel.

In some embodiments, the microstructured surface includes a regularly repeating pattern of microscopic features. In some embodiments, a microstructured surface includes microscopic features that are not arranged in regularly repeating patterns.

As used herein, a polydiorganosiloxane polyamide containing material is a material that includes one or more polydiorganosiloxane polyamides. Thus, at least a portion of the material, and in certain embodiments all of the material, includes one or more polydiorganosiloxane polyamides. In some embodiments the polydiorganosiloxane polyamides can be elastomeric. In certain embodiments, polydiorganosiloxane polyamides can be thermoplastic elastomers. For example, the polydiorganosiloxane polyamides can be polydiorganosiloxane polyamide block copolymers.

Polydiorganosiloxane polyamide block copolymers can be linear or branched. As used herein, the term "branched" is used to refer to a polymer chain having branch points that connect three or more chain segments. Examples of branched polymers include long chains having occasional and usually short branches including the same repeat units as the main chain (nominally termed a branched polymer). Branched polydiorganosiloxane polyamide block copolymers can optionally form cross-linked networks.

Polydiorganosiloxane polyamide block copolymers can have many of the desirable features of polysiloxanes such as low glass transition temperatures, thermal and oxidative stability, resistance to ultraviolet radiation, low surface energy and hydrophobicity, and high permeability to many gases. Additionally, the copolymers can have improved mechanical strength and elastomeric properties compared to polysiloxanes and linear polydiorganosiloxane polyamide block copolymers. At least some of the copolymers are optically clear, have a low refractive index, or both.

An exemplary polydiorganosiloxane polyamide block copolymer contains at least one repeat unit of Formula I-a:

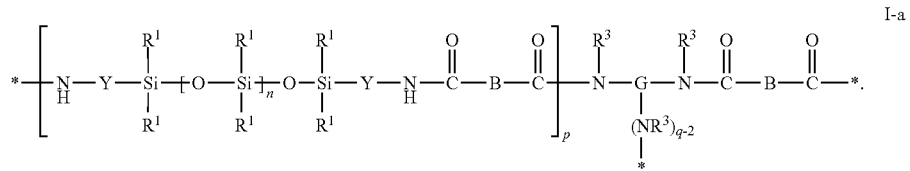

In this formula, each $R^1$ is independently an alkyl, haloalkyl, aralkyl, alkenyl, aryl, or aryl substituted with an alkyl, alkoxy, or halo. G is a residue unit equal to the formula $G(NHR^3)_q$ minus the q-$NHR^3$ groups, and q is an integer greater than or equal to 2. In certain embodiments q can, for example, be equal to 2, 3, or 4. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN$-G-$NHR^3$ is piperazine or the like). Each Y is independently an alkylene, aralkylene, or a combination thereof. Subscript n is independently an integer of 0 to 1500 and the subscript p is an integer of 1 to 10. Each B is independently a covalent bond, an alkylene of 4-20 carbons, an aralkylene, an arylene, or a combination thereof. When each group B is a covalent bond, the polydiorganosiloxane polyamide block copolymer having repeat units of Formulas I-a is referred to as a polydiorganosiloxane polyoxamide block copolymer, and preferably has repeat unit of Formulas I-b as shown below. Each asterisk (*) indicates a site of attachment of the repeat unit to another group in the copolymer such as, for example, another repeat unit of Formula I (I-a or I-b).

A preferred polydiorganosiloxane polyoxamide block copolymer contains at least one repeat unit of Formula I-b:

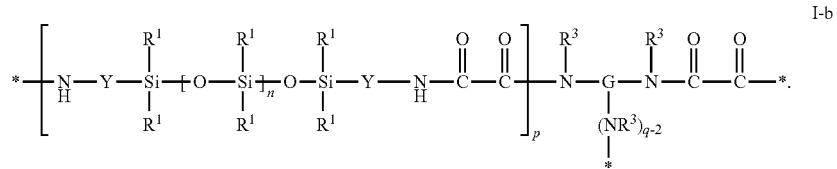

In this formula, each $R^1$ is independently an alkyl, haloalkyl, aralkyl, alkenyl, aryl, or aryl substituted with an alkyl, alkoxy, or halo. G is a residue unit equal to the formula $G(NHR^3)_q$ minus the q-$NHR^3$ groups, and q is an integer greater than or equal to 2. In certain embodiments q can, for example, be equal to 2, 3, or 4. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN$-G-$NHR^3$ is piperazine or the like). Each Y is independently an alkylene, aralkylene, or a combination thereof. Subscript n is independently an integer of 0 to 1500 and the subscript p is an integer of 1 to 10. Each asterisk (*) indicates a site of attachment of the repeat unit to another group in the copolymer such as, for example, another repeat unit of Formula I (I-a or I-b).

Suitable alkyl groups for $R^1$ in Formula I (I-a or I-b) typically have 1 to 10, 1 to 6, or 1 to 4 carbon atoms. Exemplary alkyl groups include, but are not limited to, methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^1$ often have 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable aralkyl groups for $R^1$ usually have an alkylene group with 1 to 10 carbon atoms and an aryl group with 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl where an alkylene is bonded to a phenyl group).

In some repeat units of Formula I (I-a or I-b), all $R^1$ groups can be one of alkyl, haloalkyl, aralkyl, alkenyl, aryl, or aryl substituted with an alkyl, alkoxy, or halo (e.g., all $R^1$ Groups are an alkyl such as methyl or an aryl such as phenyl). In some compounds of Formula I, the $R^1$ groups are mixtures of two or more selected from the group consisting of alkyl, haloalkyl, aralkyl, alkenyl, aryl, and aryl substituted with an alkyl, alkoxy, or halo in any ratio. Thus, for example, in certain compounds of Formula I, 0%, 1%, 2%, 5%, 10%, 20%, 30%, 40%, 50%, 60%, 70%, 80%, 90%, 95%, 98%, 99%, or 100% of the $R^1$ groups can be methyl; and 100%, 99%, 98%, 95%, 90%, 80%, 70%, 60%, 50%, 40%, 30%, 20%, 10%, 5%, 2%, 1%, or 0% of the $R^1$ groups can be phenyl.

In some repeat units of Formula I (I-a or I-b), at least 50 percent of the $R^1$ groups are methyl. For example, at least 60 percent, at least 70 percent, at least 80 percent, at least 90 percent, at least 95 percent, at least 98 percent, or at least 99 percent of the $R^1$ groups can be methyl. The remaining $R^1$ groups can be selected from an alkyl having at least two carbon atoms, haloalkyl, aralkyl, alkenyl, aryl, or aryl substituted with an alkyl, alkoxy, or halo.

Each Y in Formula I (I-a or I-b) is independently an alkylene, aralkylene, or a combination thereof. Suitable alkylene groups typically have up to 10 carbon atoms, up to 8 carbon atoms, up to 6 carbon atoms, or up to 4 carbon atoms. Exemplary alkylene groups include methylene, ethylene, propylene, butylene, and the like. Suitable aralkylene groups usually have an arylene group with 6 to 12 carbon atoms bonded to an alkylene group with 1 to 10 carbon atoms. In some exemplary aralkylene groups, the arylene portion is phenylene. That is, the divalent aralkylene group is phenylene-alkylene where the phenylene is bonded to an alkylene having 1 to 10, 1 to 8, 1 to 6, or 1 to 4 carbon atoms. As used herein with reference to group Y, "a combination thereof" refers to a combination of two or more groups selected from an alkylene and aralkylene group. A combination can be, for example, a single aralkylene bonded to a single alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each subscript n in Formula I (I-a or I-b) is independently an integer of 0 to 1500. For example, subscript n can be an integer up to 1000, up to 500, up to 400, up to 300, up to 200, up to 100, up to 80, up to 60, up to 40, up to 20, or up to 10. The value of n is often at least 1, at least 2, at least 3, at least 5, at least 10, at least 20, or at least 40. For example, subscript n can be in the range of 40 to 1500, 0 to 1000, 40 to 1000, 0 to 500, 1 to 500, 40 to 500, 1 to 400, 1 to 300, 1 to 200, 1 to 100, 1 to 80, 1 to 40, or 1 to 20.

The subscript p is an integer of 1 to 10. For example, the value of p is often an integer up to 9, up to 8, up to 7, up to 6, up to 5, up to 4, up to 3, or up to 2. The value of p can be in the range of 1 to 8, 1 to 6, or 1 to 4.

Group G in Formula I (I-a or I-b) is a residual unit that is equal to a diamine or polyamine compound of formula $G(NHR^3)_q$ minus the q amino groups (i.e., $-NHR^3$ groups), where q is an integer greater than or equal to 2. The diamine and/or polyamine can have primary and/or secondary amino groups. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN-G-NHR^3$ is piperazine). In most embodiments, $R^3$ is hydrogen or an alkyl. In many embodiments, all of the amino groups of the diamine and/or polyamine are primary amino groups (i.e., all the $R^3$ groups are hydrogen) and the diamine and/or polyamine are of the formula $G(NH_2)_q$ (e.g., a diamine of the formula $R^3HN-G-NHR^3$ when q=2).

In certain embodiments, Group G in Formula I (I-a or I-b) is a mixture of residual units that are equal to (i) a diamine compound of the formula $R^3HN-G-NHR^3$ minus the two amino groups (i.e., $-NHR^3$ groups) and (ii) a polyamine compound of the formula $G(NHR^3)_q$ minus the q amino groups (i.e., $-NHR^3$ groups), where q is an integer greater than 2. In such embodiments, the polyamine compound of formula $G(NHR^3)_q$ can be, but is not limited to, triamine compounds (i.e., q=3), tetraamine compounds (i.e., q=4), and combinations thereof. In such embodiments, the number of equivalents of polyamine (ii) per equivalent of diamine (i) is preferably at least 0.001, more preferably at least 0.005, and most preferably at least 0.01. In such embodiments, the number of equivalents of polyamine (ii) per equivalent of diamine (i) is preferably at most 3, more preferably at most 2, and most preferably at most 1.

When G includes residual units that are equal to (i) a diamine compound of formula $R^3HN-G-NHR^3$ minus the two amino groups (i.e., $-NHR^3$ groups), G can be an alkylene, heteroalkylene, polydiorganosiloxane, arylene, aralkylene, or a combination thereof. Suitable alkylenes often have 2 to 10, 2 to 6, or 2 to 4 carbon atoms. Exemplary alkylene groups include ethylene, propylene, butylene, and the like. Suitable heteroalkylenes are often polyoxyalkylenes such as polyoxyethylene having at least 2 ethylene units, polyoxypropylene having at least 2 propylene units, or copolymers thereof. Suitable polydiorganosiloxanes include polydiorganosiloxane diamines, minus the two amino groups. Exemplary polydiorganosiloxanes include, but are not limited to, polydimethylsiloxanes with alkylene Y groups. Suitable aralkylene groups usually contain an arylene group having 6 to 12 carbon atoms bonded to an alkylene group having 1 to 10 carbon atoms. Some exemplary aralkylene groups are phenylene-alkylene where the phenylene is bonded to an alkylene having 1 to 10 carbon atoms, 1 to 8 carbon atoms, 1 to 6 carbon atoms, or 1 to 4 carbon atoms. As used herein with reference to group G, "a combination thereof" refers to a combination of two or more groups selected from an alkylene, heteroalkylene, polydiorganosiloxane, arylene, and aralkylene. A combination can be, for example, an aralkylene bonded to an alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

In preferred embodiments, the polydiorganosiloxane polyamide is a polydiorganosiloxane polyoxamide. The polydiorganosiloxane polyoxamide tends to be free of groups having a formula —$R^a$—(CO)—NH— where $R^a$ is an alkylene. All of the carbonylamino groups along the backbone of the copolymeric material are part of an oxalylamino group (i.e., the —(CO)—(CO)—NH— group). That is, any carbonyl group along the backbone of the copolymeric material is bonded to another carbonyl group and is part of an oxalyl group. More specifically, the polydiorganosiloxane polyoxamide has a plurality of aminoxalylamino groups.

The polydiorganosiloxane polyamide can be a block copolymer and can be an elastomeric material. Unlike many of the known polydiorganosiloxane polyamides that are generally formulated as brittle solids or hard plastics, the polydiorganosiloxane polyamides can be formulated to include greater than 50 weight percent polydiorganosiloxane segments based on the weight of the copolymer. The weight percent of the diorganosiloxane in the polydiorganosiloxane polyamides can be increased by using higher molecular weight polydiorganosiloxanes segments to provide greater than 60 weight percent, greater than 70 weight percent, greater than 80 weight percent, greater than 90 weight percent, greater than 95 weight percent, or greater than 98 weight percent of the polydiorganosiloxane segments in the polydiorganosiloxane polyamides. Higher amounts of the polydiorganosiloxane can be used to prepare elastomeric materials with lower modulus while maintaining reasonable strength.

Some of the polydiorganosiloxane polyamides can be heated to a temperature up to 200° C., up to 225° C., up to 250° C., up to 275° C., or up to 300° C. without noticeable degradation of the material. For example, when heated in a thermogravimetric analyzer in the presence of air, the copolymers often have less than a 10 percent weight loss when scanned at a rate 50° C. per minute in the range of 20° C. to 350° C. Additionally, the copolymers can often be heated at a temperature such as 250° C. for 1 hour in air without apparent degradation as determined by no detectable loss of mechanical strength upon cooling.

The copolymeric material having repeat units of Formula I (I-a or I-b) can be optically clear. As used herein, the term "optically clear" refers to a material that is clear to the human eye. An optically clear copolymeric material often has a luminous transmission of at least 90 percent, a haze of less than 2 percent, and opacity of less than 1 percent in the 400 to 700 nm wavelength range. Both the luminous transmission and the haze can be determined using, for example, the method of ASTM-D 1003-95.

Additionally, the copolymeric material having repeat units of Formula I (I-a or I-b) can have a low refractive index. As used herein, the term "refractive index" refers to the absolute refractive index of a material (e.g., copolymeric material) and is the ratio of the speed of electromagnetic radiation in free space to the speed of the electromagnetic radiation in the material of interest. The electromagnetic radiation is white light. The index of refraction is measured using an Abbe refractometer, available commercially, for example, from Fisher Instruments of Pittsburgh, Pa. The measurement of the refractive index can depend, to some extent, on the particular refractometer used. For some embodiments (e.g., embodiments in which the copolymer includes a polydimethylsiloxane segment), the copolymeric material can have a refractive index in the range of 1.41 to 1.50. For some other embodiments (e.g., embodiments in which the copolymer includes a polyphenylsiloxane or a polydiphenylsiloxane segment), the copolymeric material can have a refractive index in the range of from 1.46 to 1.55.

Polydiorganosiloxane polyamide block copolymers can optionally have amide end-capped (e.g., oxalated) organic soft segments. In addition to at least one repeat unit of Formula I-a, such polymers can optionally include at least one repeat unit of Formula II-a:

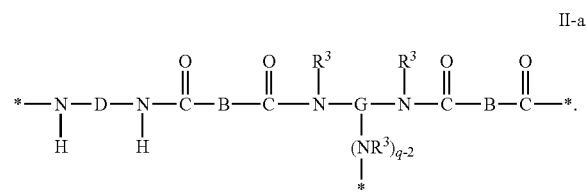

In this formula, $R^3$, G, B, *, and q are as defined herein above, and D is an organic soft segment residue. Each D is Formula II (II-a or II-b) represents an organic soft segment. Organic soft segments typically include one or more polyether residues such as, for example, polyoxyethylene residues, polyoxypropylene residues, poly(oxyethylene-co-oxypropylene) residues, and combinations thereof. The organic soft segment preferably has an average molecular weight of at least 450, more preferably at least 700, and most preferably at least 2000. The organic soft segment preferably has an average molecular weight of at most 8000, more preferably at most 6000, and most preferably at most 4000. A wide variety of organic soft segments can be used including, for example, those described in U.S. Pat. No. 4,119,615 (Schulze).

Polydiorganosiloxane polyamides such as polydiorganosiloxane polyamide block copolymers and polydiorganosiloxane polyoxamide block copolymers can be prepared by methods known in the art. See, for example, U.S. Patent Application Publication Nos. 2007/0148474 A1 (Leir et al.) and 2007/0149745 A1 (Leir et al.), and U.S. application Ser. Nos. 11/821,571, 11/821,572, 11/821,575, and 11/821,596, all filed Jun. 22, 2007.

Polydiorganosiloxane polyamide copolymers can be blended with one or more other polymers (e.g., organic polymer components) such as a hot melt processable thermoplastic polymer (which may be elastomeric or nonelastomeric), a hot melt processable elastomeric thermoset polymer, a silicone polymer, and mixtures thereof. See, for example, U.S. Patent Application Publication No. 2007/0148475 A1 (Sherman et al.), and U.S. application Ser. No. 11/821,568, filed Jun. 22, 2007.

The organic polymer may be solvent or melt mixed with the polydiorganosiloxane polyamide segmented copolymer. The organic polymer may be a polydiorganosiloxane polyamide-containing component or a polymer that does not contain polydiorganosiloxane segments.

Examples of suitable polydiorganosiloxane polyamide-containing components include linear and/or branched polydiorganosiloxane polyamide copolymers. An exemplary linear copolymeric material contains at least two repeat units of Formula III-a:

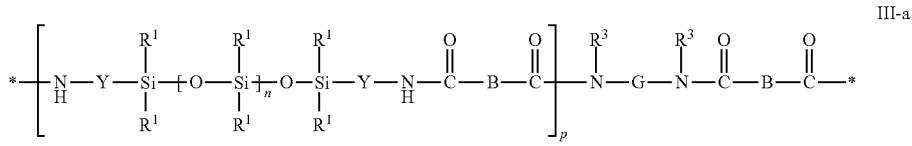

III-a

In this formula, each $R^1$ is independently an alkyl, haloalkyl, aralkyl, alkenyl, aryl, or aryl substituted with an alkyl, alkoxy, or halo. Each Y is independently an alkylene, aralkylene, or a combination thereof. Subscript n is independently an integer of 0 to 1500 and subscript p is an integer of 1 to 10. Group G is a divalent group that is the residue unit that is equal to a diamine of formula $R^3HN\text{-}G\text{-}NHR^3$ minus the two —$NHR^3$ groups (i.e., amino groups). Group $R^3$ is hydrogen or alkyl or $R^3$ taken together with G and with the nitrogen to which they are both attached forms a heterocyclic group. Each B is independently a covalent bond, an alkylene of 4-20 carbons, an aralkylene, an arylene, or a combination thereof. Each asterisk indicates the position of attachment of the repeating unit to another group such as another repeat unit.

A preferred copolymeric material contains at least two repeat units of Formula III-b:

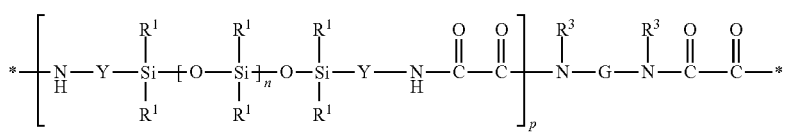

III-b

In this formula, each $R^1$ is independently an alkyl, haloalkyl, aralkyl, alkenyl, aryl, or aryl substituted with an alkyl, alkoxy, or halo. Each Y is independently an alkylene, aralkylene, or a combination thereof. Subscript n is independently an integer of 0 to 1500 and subscript p is an integer of 1 to 10. Group G is a divalent group that is the residue unit that is equal to a diamine of formula $R^3HN\text{-}G\text{-}NHR^3$ minus the two —$NHR^3$ groups (i.e., amino groups). Group $R^3$ is hydrogen or alkyl or $R^3$ taken together with G and with the nitrogen to which they are both attached forms a heterocyclic group. Each asterisk indicates the position of attachment of the repeating unit to another group such as another repeat unit.

Thermoplastic materials useful in the present invention that are generally considered nonelastomeric include, for example, polyolefins such as isotactic polypropylene, low density polyethylene, linear low density polyethylene, very low density polyethylene, medium density polyethylene, high density polyethylene, polybutylene, nonelastomeric polyolefin copolymers or terpolymers, such as ethylene/propylene copolymer and blends thereof, ethylene-vinyl acetate copolymers such as that available under the trade designation ELVAX 260, available from DuPont Chemical Co.; ethylene acrylic acid copolymers; ethylene methacrylic acid copolymers such as that available under the trade designation SURLYN 1702, available from DuPont Chemical Co.; polymethylmethacrylate; polystyrene; ethylene vinyl alcohol; polyester; amorphous polyester; polyamides; fluorinated thermoplastics, such a polyvinylidene fluoride, polytetrafluoroethylene, fluorinated ethylene/propylene copolymers and fluorinated ethylene/propylene copolymers; halogenated thermoplastics, such as a chlorinated polyethylene. Any single thermoplastic material can be mixed with at least one branched polydiorganosiloxane polyamide-containing component. Alternatively, a mixture of thermoplastic materials may be used.

Thermoplastic materials that have elastomeric properties are typically called thermoplastic elastomeric materials. Thermoplastic elastomeric materials are generally defined as materials that act as though they were covalently cross-linked, exhibiting high resilience and low creep, yet flow when heated above their softening point. Thermoplastic elastomeric materials useful in the present invention include, for example, linear, radial, star and tapered styrene-isoprene block copolymers such as that available under the trade designation KRATON D1107P from Shell Chemical Co. of Houston, Tex. and that available under the trade designation EUROPRENE SOL TE 9110 from EniChem Elastomers Americas, Inc. of Houston, Tex.; linear styrene-(ethylene-butylene) block copolymers such as that available under the trade designation KRATON G1657 from Shell Chemical Co.; linear styrene-(ethylene-propylene) block copolymers such as that available under the trade designation KRATON G1657X from Shell Chemical Co.; linear, radial, and star styrene-butadiene block copolymers such as that available under the trade designation KRATON D1118X from Shell Chemical Co. and that available under the trade designation EUROPRENE SOL TE 6205 from EniChem Elastomers Americas, Inc.; polyetheresters such as that available under the trade designation HYTREL G3548 from DuPont, elastomeric ethylene-propylene copolymers; thermoplastic elastomeric polyurethanes such as that available under the trade designation MORTHANE URETHENE PE44-203 from Morton International, Inc., Chicago, Ill.; self-tacky or tackified polyacrylates including $C_3$ to $C_{12}$ alkylesters that may contain other comonomers, such as for example, isooctyl acrylate and from 0 to 20 weight percent acrylic acid; polyvinylethers; poly-α-olefin-based thermoplastic elastomeric materials such as those represented by the formula —$(CH_2CHR)_x$ where R is an alkyl group containing 2 to 10 carbon atoms and poly-α-olefins based on metallocene catalysis such as that available under the trade designation ENGAGE EG8200, an ethylene/poly-α-olefin copolymer, available from Dow Plastics Co. of Midland, Mich.; as well as polydiorganosiloxane polyurea-urethanes, available from Wacker Chemie AG, Germany under the trade designation GENIOMER.

Thermoset elastomers (i.e., elastomeric thermosets) are materials that change irreversibly under the influence of heat from a fusible and soluble material into one that is infusible and insoluble through the formation of a covalently cross-linked, thermally stable network. Thermoset elastomers useful in the present invention include, for example, natural rubbers such as CV-60, a controlled viscosity grade available from Goodyear Chemical, Akron, Ohio, and SMR-5, a ribbed smoked sheet rubber; butyl rubbers, such as Exxon Butyl 268 available from Exxon Chemical Co.; synthetic polyisoprenes such as that available under the trade designation CARIFLEX IR309 from Royal Dutch Shell of Netherlands and that available under the trade designation NATSYN 2210 from Goodyear Tire and Rubber Co.; styrene-butadiene random copolymer rubbers such as that available under the trade designation AMERIPOL 1011A from BF Goodrich of Akron, Ohio; polybutadienes; polyisobutylenes such as that available under the trade designation VISTANEX MM L-80 from Exxon Chemical Co.; polyurethanes such as, for example, polyoctadecyl carbamate disclosed in U.S. Pat. No. 2,532,011 (Dahlquist et al.); amorphous poly-α-olefins such as $C_4$-$C_{10}$ linear or branched poly-α-olefins; polydiorganosiloxane polyurea-containing components, such as those disclosed in U.S. Pat. No. 5,214,119 (Leir et al.).

Suitable silicone polymers are typically fluids and may be curable (through incorporation of suitable functional groups such as hydroxyl groups or ethylenically unsaturated groups, e.g., acrylate groups) or substantially noncurable. Examples of suitable silicone fluids are described in, for example, International Application Publication No. WO 97/40103 (Paulick et al.), U.S. Pat. No. 5,091,483 (Mazurek et al.) and U.S. Pat. No. 6,441,118 (Sherman et al.), and U.S. Patent Application Publication No. 2005/0136266 (Zhou et al.). Particularly preferred silicone polymers are moisture-curable silicone fluids, e.g., hydroxyl-terminated polydiorganosiloxanes or nonreactive silicone fluids such as that available under the trade designation 47V1000 RHODORSIL from Rhodia Silicones. Any of the hydroxyl-terminated polydiorganosiloxanes typically used in known silicone sealing and adhesive compositions may be used in the compositions of the present invention. Examples of suitable commercially available silicone fluids include those available under the trade designation MASIL from Lubruzol Corp. (Ohio) and Wacker Chemie AG (Germany).

Compositions and constructions as disclosed herein can also include functional components. Functional components such as antistatic additives, ultraviolet light absorbers (UVAs), hindered amine light stabilizers (HALS), dyes, colorants, pigments, antioxidants, slip agents, low adhesion materials, conductive materials, abrasion resistant materials, optical elements, dimensional stabilizers, adhesives, tackifiers, flame retardants, phosphorescent materials, fluorescent materials, nanoparticles, anti-graffiti agents, dew-resistant agents, load bearing agents, silicate resins, fumed silica, glass beads, glass bubbles, glass fibers, mineral fibers, clay particles, organic fibers, e.g., nylon, KEVLAR, metal particles, and the like which can be added in amounts up to 100 parts per 100 parts of the sum of the branched polydiorganosiloxane polyamide segmented polymeric component, provided that if and when incorporated, such additives are not detrimental to the function and functionality of the final polymer product. Other additives such as light diffusing materials, light absorptive materials and optical brighteners, flame retardants, stabilizers, antioxidants, compatibilizers, antimicrobial agents such as zinc oxide, electrical conductors, thermal conductors such as aluminum oxide, boron nitride, aluminum nitride, and nickel particles, including organic and/or inorganic particles, or any number or combination thereof can be blended into these systems. The functional components listed above may also be incorporated into polydiorganosiloxane polyamide block copolymer provided such incorporation does not adversely affect any of the resulting product to an undesirable extent.

Fillers, tackifiers, plasticizers, and other property modifiers may be incorporated in the branched, polydiorganosiloxane polyamide segmented organic polymer. Tackifying materials or plasticizers useful with the polymeric materials are preferably miscible at the molecular level, e.g., soluble in, any or all of the polymeric segments of the elastomeric material or the thermoplastic elastomeric material. These tackifying materials or plasticizers are generally immiscible with the polydiorganosiloxane polyamide-containing component. When the tackifying material is present it generally comprises 5 to 300 parts by weight, more typically up to 200 parts by weight, based on 100 parts by weight of the polymeric material. Examples of tackifiers suitable for the invention include but are not limited to liquid rubbers, hydrocarbon resins, rosin, natural resins such as dimerized or hydrogenated balsams and esterified abietic acids, polyterpenes, terpene phenolics, phenol-formaldehyde resins, and rosin esters. Examples of plasticizers include but are not limited to polybutene, paraffinic oils, petrolatum, and certain phthalates with long aliphatic side chains such as ditridecyl phthalate.

Either pressure sensitive adhesives or heat activated adhesives can be formulated by combining the polydiorganosiloxane polyoxamides with a tackifier such as a silicate tackifying resin. As used herein, the term "pressure sensitive adhesive" refers to an adhesive that possesses the following properties: (1) aggressive and permanent tack; (2) adherence to a substrate with no more than finger pressure; (3) sufficient ability to hold onto an adherend; and (4) sufficient cohesive strength to be removed cleanly from the adherend. As used herein, the term "heat activated adhesive" refers to an adhesive composition that is essentially non-tacky at room temperature but that becomes tacky above room temperature above an activation temperature such as above 30° C. Heat activated adhesives typically have the properties of a pressure sensitive adhesive above the activation temperature.

Tackifying resins such as silicate tackifying resins are added to the polydiorganosiloxane polyoxamide copolymer to provide or enhance the adhesive properties of the copolymer. The silicate tackifying resin can influence the physical properties of the resulting adhesive composition. For example, as silicate tackifying resin content is increased, the glassy to rubbery transition of the adhesive composition occurs at increasingly higher temperatures. In some exemplary adhesive compositions, a plurality of silicate tackifying resins can be used to achieve desired performance.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000 or in the range of 500 to 15,000 and generally have methyl R' groups.

MQ silicate tackifying resins are copolymeric resins having $R'_3SiO_{1/2}$ units ("M" units) and $SiO_{4/2}$ units ("Q" units), where the M units are bonded to the Q units, each of which is bonded to at least one other Q unit. Some of the $SiO_{4/2}$ units ("Q" units) are bonded to hydroxyl radicals resulting in $HOSiO_{3/2}$ units ("$T^{OH}$" units), thereby accounting for the silicon-bonded hydroxyl content of the silicate tackifying resin, and some are bonded only to other $SiO_{4/2}$ units.

Such resins are described in, for example, *Encyclopedia of Polymer Science and Engineering*, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248, 739 (Schmidt et al.). Other examples are disclosed in U.S. Pat. No. 5,082,706 (Tangney). The above-described resins are generally prepared in solvent. Dried or solventless, M silicone tackifying resins can be prepared, as described in U.S. Pat. No. 5,319,040 (Wengrovius et al.), U.S. Pat. No. 5,302, 685 (Tsumura et al.), and U.S. Pat. No. 4,935,484 (Wolfgruber et al.).

Certain MQ silicate tackifying resins can be prepared by the silica hydrosol capping process described in U.S. Pat. No. 2,676,182 (Daudt et al.) as modified according to U.S. Pat. No. 3,627,851 (Brady), and U.S. Pat. No. 3,772,247 (Flannigan). These modified processes often include limiting the concentration of the sodium silicate solution, and/or the silicon-to-sodium ratio in the sodium silicate, and/or the time before capping the neutralized sodium silicate solution to generally lower values than those disclosed by Daudt et al. The neutralized silica hydrosol is often stabilized with an alcohol, such as 2-propanol, and capped with $R_3SiO_{1/2}$ siloxane units as soon as possible after being neutralized. The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having $R'_3SiO_{1/2}$ units ("M" units), $SiO_{4/2}$ units ("Q" units), and $R'_2SiO_{2/2}$ units ("D" units) such as are taught in U.S. Pat. No. 2,736,721 (Dexter). In MQD silicone tackifying resins, some of the methyl R' groups of the $R'_2SiO_{2/2}$ units ("D" units) can be replaced with vinyl ($CH_2=CH-$) groups ("$D^{Vi}$" units).

MQT silicate tackifying resins are terpolymers having $R'_3SiO_{1/2}$ units, $SiO_{4/2}$ units and $R'SiO_{3/2}$ units ("T" units) such as are taught in U.S. Pat. No. 5,110,890 (Butler) and Japanese Kokai HE 2-36234.

Suitable silicate tackifying resins are commercially available from sources such as Dow Corning, Midland, Mich., General Electric Silicones Waterford, N.Y. and Rhodia Silicones, Rock Hill, S.C. Examples of particularly useful MQ silicate tackifying resins include those available under the trade designations SR-545 and SR-1000, both of which are commercially available from GE Silicones, Waterford, N.Y. Such resins are generally supplied in organic solvent and may be employed in the formulations of the adhesives of the present invention as received. Blends of two or more silicate resins can be included in the adhesive compositions.

The adhesive compositions typically contain 20 to 80 weight percent polydiorganosiloxane polyoxamide and 20 to 80 weight percent silicate tackifying resin based on the combined weight of polydiorganosiloxane polyoxamide and silicate tackifying resin. For example, the adhesive compositions can contain 30 to 70 weight percent polydiorganosiloxane polyoxamide and 30 to 70 weight percent silicate tackifying resin, 35 to 65 weight percent polydiorganosiloxane polyoxamide and 35 to 65 weight percent silicate tackifying resin, 40 to 60 weight percent polydiorganosiloxane polyoxamide and 40 to 60 weight percent silicate tackifying resin, or 45 to 55 weight percent polydiorganosiloxane polyoxamide and 45 to 55 weight percent silicate tackifying resin.

The adhesive composition can be solvent-free or can contain a solvent. Suitable solvents include, but are not limited to, toluene, tetrahydrofuran, dichloromethane, aliphatic hydrocarbons (e.g., alkanes such as hexane), or mixtures thereof.

Polydiorganosiloxane polyamides with a small amount of branching can be soluble in many common organic solvents such as, for example, toluene, tetrahydrofuran, dichloromethane, aliphatic hydrocarbons (e.g., alkanes such as hexane), or mixtures thereof. Polydiorganosiloxane polyamides with higher amounts of branching can be swellable in many common organic solvents such as, for example, toluene, tetrahydrofuran, dichloromethane, aliphatic hydrocarbons (e.g., alkanes such as hexane), or mixtures thereof.

The polydiorganosiloxane polyamides can be cast from solvents as film, molded or embossed in various shapes, or extruded into films. The high temperature stability of the copolymeric material makes them well suited for extrusion methods of film formation. The films can be optically clear. A multilayer film containing the polydiorganosiloxane polyamide block copolymers is further described in U.S. Patent Application Publication No. 2007/0177272 A1 (Benson et al.).

In one or more embodiments, a polydiorganosiloxane polyamide containing material having a structured surface can spontaneously and uniformly transport liquids along the axis of channels. Two general factors that can influence the ability of a polydiorganosiloxane polyamide containing material having a structured surface to spontaneously transport liquids (e.g., aqueous fluids and non-aqueous fluids such as organic fluids, silicone fluids, fluorocarbon fluids, and combinations thereof) are (i) the geometry or topography of the surface (e.g., capillarity, shape of the channels) and (ii) the nature of the film surface (e.g., surface energy). To achieve the desired amount of fluid transport capability, the structure or topography of the microstructured surface can be adjusted and/or the surface energy of the microstructured surface can be adjusted. In order for a closed channel wick made from a microstructured surface to function it can be sufficiently hydrophilic to allow the desired fluid to wet the surface. Generally, to facilitate spontaneous wicking in open channels, the fluid must wet the surface of the microstructured surface, and the contact angle must be equal to or less than 90 degrees minus one-half the notch angle, as is described hereinafter.

Generally, the susceptibility of a solid surface to be wet out by a liquid is characterized by the contact angle that the liquid makes with the solid surface after being deposited on the horizontally disposed surface and allowed to stabilize thereon. It is sometimes referred to as the "static equilibrium contact angle," and herein referred to as "contact angle."

As shown in FIGS. 1a and 1b, the contact angle theta is the angle between a line tangent to the surface of a bead of liquid on a surface at its point of contact to the surface and the plane of the surface. A bead of liquid whose tangent was perpendicular to the plane of the surface would have a contact angle of 90 degrees.

Typically, if the contact angle is 90 degrees or less, as shown in FIG. 1a, the solid surface is considered to be wet by the liquid. Surfaces on which drops of water or aqueous solutions exhibit a contact angle of less than 90 degrees are commonly referred to as "hydrophilic." As used herein, "hydrophilic" is used only to refer to the surface characteristics of a material, i.e., that it is wet by aqueous solutions, and does not express whether or not the material absorbs aqueous solutions.

Accordingly, a material can be referred to as hydrophilic whether or not a sheet of the material is impermeable or permeable to aqueous solutions. Thus, hydrophilic microstructured surfaces can be formed from materials that are inherently hydrophilic. Liquids that yield a contact angle of near zero on a surface are considered to completely wet out the surface. The contact angle of an inherently hydrophobic material with water is typically greater than 90 degrees, such as shown in FIG. 1b.

Microscopic features of a microstructured surface can have a wide variety of geometries. In one or more embodiments, a microscopic feature in a microstructured surface substantially retains its geometry and surface characteristics upon exposure to liquids. The microstructured surface can also be treated to render the surface biocompatible. For example, a heparin coating can be applied to the surface.

The channels in microstructured surfaces can have a wide variety of geometries that provide for desired liquid transport properties. In one or more embodiments, the channels in the microstructured surface provide desired liquid transport and are readily replicated.

Microscopic features can be in the shape of a channel (e.g., a groove) in the surface of a material. The cross section of such a channel can have a wide variety of shapes (e.g., rectangular, V-shaped, round, etc.). Channels can also have cross-sections that are more complex shapes and can have grooves within grooves. Some examples of cross-sectional shapes of channels that can be used in a device according to the present disclosure are described in U.S. Pat. No. 6,420,622 (Johnston et al.).

The microstructured surfaces can have a variety of topographies. For example, microstructured surfaces can include a plurality of channels with V-shaped or rectangular cross-sections, and/or combinations of these, as well as structures that have secondary channels, i.e., channels within channels. Referring to FIG. 2, for open channels, a desired surface energy of the microstructured surface of V-channeled fluid control films can be such that:

$$\text{Theta} \leq (90° - \text{Alpha}/2),$$

wherein theta ($\theta$) is the contact angle of the liquid with the film and alpha ($\alpha$) is the average included angle of the secondary V-channel notches 2 within primary channel 1.

Depending on the nature of the microstructured material itself, and the nature of the fluid being transported, one may desire to adjust or modify the microstructured surface in order to ensure sufficient capillary forces of the microstructures. For example, the microstructured surface can be modified in order to ensure it is sufficiently hydrophilic. Liquids that will come into contact with the microstructured surfaces can be aqueous. Thus, if such microstructured surfaces are used, they can be modified, e.g., by surface treatment, application of surface coatings or agents, or incorporation of selected agents, such that the surface is rendered hydrophilic so as to exhibit a contact angle of 90 degrees or less, thereby enhancing the wetting and liquid transport properties of the microstructured surface. Suitable methods of making the surface hydrophilic include: (i) incorporation of a surfactant; (ii) incorporation or surface coating with a hydrophilic polymer; (iii) treatment with a hydrophilic silane; or (iv) combinations thereof. Other methods can also be envisioned.

A wide variety of methods can be utilized to achieve a hydrophilic microstructured surface. For example, in one embodiment surface treatments can be employed to render a microstructured surface hydrophilic. Exemplary surface treatments include topical application of a surfactant, plasma treatment, vacuum deposition, polymerization of hydrophilic monomers, grafting hydrophilic moieties onto the surface, corona treatment, flame treatment, or combinations thereof. In another embodiment, a surfactant or other suitable agent can be blended with a material as an internal additive, and a surface of the material can then be structured. Exemplary surfactants and use of surfactants in fluid control devices are disclosed in, for example, U.S. Pat. No. 6,420,622 (Johnston et al.).

A microscopic feature of a microstructured surface can include, for example, a well (e.g., a reservoir). Such a feature can be useful, for example, to collect and/or retain fluids. A well can optionally be attached to a channel such that a fluid can flow from one into the other. For example, a well can receive fluids from one or more channels, provide fluids to one or more channels, or both. A well can have the same depth as a channel or can have a different depth.

Referring now to FIG. 3, in one or more embodiments of the present disclosure, a device 5 includes a polydiorganosiloxane polyamide containing material 30 and has at least one microstructured surface 10 (microscopic features not shown). The device 5 can include more than one microstructured surface 10.

Referring to FIG. 4, in some embodiments, a device 100 can include a material 130 that includes a polydiorganosiloxane polyamide containing material and has two major surfaces 110 and 120. In one or more embodiments, at least one major surface (110 and/or 120) of material 130 is a structured (e.g., microstructured) surface. In one or more embodiments, the device 100 can include a plurality of materials 130 that include a polydiorganosiloxane polyamide containing material (e.g., layers of material), with one, some, or all of the materials 130 having a microstructured surface. Microstructured surfaces of materials 130 can each include the same or different channel configurations and/or number of channels, depending on a particular application.

In one or more embodiments, the microstructured surface of the polydiorganosiloxane polyamide containing material includes at least one microscopic feature. Such microscopic features include, but are not limited to, grooves, wells, and other architectures that can project out of and/or into the polydiorganosiloxane polyamide containing material.

In some embodiments, at least a portion of a microstructured surface 110 and/or 120 of a polydiorganosiloxane polyamide containing material can have hydrophilic characteristics. In other embodiments, at least a portion of a microstructured surface 110 and/or 120 of a polydiorganosiloxane polyamide containing material can have hydrophobic characteristics. Surface properties of a polydiorganosiloxane polyamide containing material can be modifiable to accommodate applications ranging in need from hydrophobic to hydrophilic.

Referring to FIG. 5, in some embodiments, a device can be a fluid handling device 200 that includes a polydiorganosiloxane polyamide containing material 230 attached to a substrate 220. The substrate 220 can be attached to a structured surface 210 of polydiorganosiloxane polyamide containing material 230. In such cases, the structured surface 210 of polydiorganosiloxane polyamide containing material 230 and substrate 220 can, for example, form a fluid handling device 200. Such a fluid handling device 200 can, for example, be a structured capillary device (i.e., having capillary-shaped structures or micro structures).

In some embodiments, a substrate 220, which is attached to polydiorganosiloxane polyamide containing material 230, includes conductive material (e.g., integrated circuitry). For example, the substrate can be a flexible circuit (i.e., a "flex circuit"), such as, for example, a film-based flexible circuit.

Referring to FIG. 6, another aspect of the present disclosure is a fluid handling device 300 including a flex circuit 320. The flex circuit 320 is attached to a structured material that includes polydiorganosiloxane polyamide containing material 330. The polydiorganosiloxane polyamide containing material 330 can have a major surface having features, e.g., a structured surface 310. In some embodiments, the flex circuit 320 is attached to the structured (e.g., microstructured) surface 310 of the polydiorganosiloxane polyamide containing material 330.

Flex circuits generally include a flexible polymeric substrate material having a quantity of a conductive material thereon or therein. A wide variety of polymeric materials having suitable flexible circuit substrate properties (e.g., dimensional stability, thermal resistance, tear resistance, and/or flexibility) can be used. For example, a polyester such as, for example, polyethylene terephthalate can be used as a substrate in certain flexible circuit applications. A wide variety of conductive materials can be used in the flexible circuit. In some embodiments, the conductive materials can include one of more non-ferrous metals. For example, in certain embodiments gold, copper, nickel, tin, lead, and/or aluminum can be used in one or more flexible circuit applications. The conductive material can take the form of integrated circuitry, useful in various applications in which circuits are used. Such applications can include, for example, fluid handling applications for use in diagnostic devices (e.g., medical diagnostic devices), testing devices (e.g., environmental testing devices such as those used, for example, in testing and/or purification of water and/or devices testing for bacteria and/or pathogens in the food industry), actuation devices (e.g., fluid driven actuation devices), and combinations thereof. In one or more embodiments of the present disclosure, devices can include none, one, or more than one flexible circuit.

Figure 7:
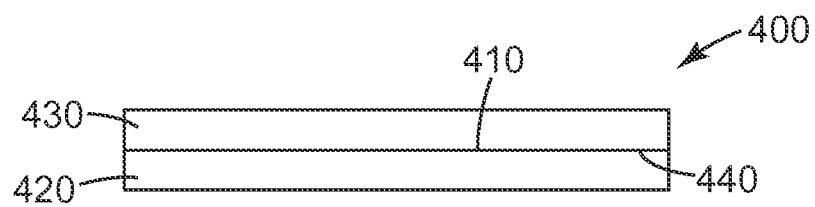
FIG. 7 is a schematic diagram of a device that includes a structured material and a substrate.

Referring to FIG. 7, in some embodiments, a device 400 includes a structured material 430, at least a portion of which is adhered directly to at least a portion of a substrate 420 that includes conductive material (not shown). Such conductive material can be integrated circuitry, as in, for example, a flex circuit. As used herein, "adhered directly" means that there are no intervening materials (e.g., layers) between structured material 430 and substrate 420. In certain embodiments, at least a portion of structured material 430 is adhered directly to at least a portion of substrate 420 without using additional adhesive. In one or more embodiments, device 400 includes no additional adhesive at the interface of structured (e.g., microstructured) surface 410 and major surface 440 of substrate 420. In certain embodiments, the interface between the structured material 430 and the substrate 420 having conductive material (e.g., integrated circuitry) can form a fluid-tight seal without using additional adhesive.

In such a device 400, substrate 420 having conductive material (e.g., integrated circuitry) can be a film-based flex circuit. A substrate 420 having integrated circuitry (e.g., a film-based flex circuit) can include a polyester substrate. An exemplary polyester substrate is a polyethylene terephthalate substrate. In some embodiments, at least a portion of a polyethylene terephthalate substrate 420 is directly adhered to at least a portion of a structured material 430 that includes one or more polydiorganosiloxane polyamides.

FIGS. 3-7 depict schematic representations of items having uniform thickness. For example, FIG. 3 depicts a polydiorganosiloxane polyamide containing material 30 having uniform thickness. However, while one or more embodiments of the present disclosure can include a polydiorganosiloxane polyamide containing material 30 having a uniform thickness or substantially uniform thickness across a given polydiorganosiloxane polyamide containing material 30, it should be noted that one or more embodiments of the present disclosure can also include a polydiorganosiloxane polyamide containing material 30 having non-uniform thickness across a given polydiorganosiloxane polyamide containing material 30. Further, in a device 100 that includes, for example, a plurality of polydiorganosiloxane polyamide containing materials 130 (e.g. a plurality of layers of polydiorganosiloxane polyamide containing materials 130), each of the plurality of polydiorganosiloxane polyamide containing materials 130 can have either uniform, substantially uniform, or non-uniform thickness across a particular polydiorganosiloxane polyamide containing material 130 and the thickness of each polydiorganosiloxane polyamide containing material 130 (e.g., layer) can be the same or different from one polydiorganosiloxane polyamide containing material 130 to another. A "substantially uniform" thickness, as used herein, is used to describe a variation in thickness across a particular polydiorganosiloxane polyamide containing material of no greater than 50%, and preferably no greater than 25%, no greater than 10%, no greater than 5%, no greater than 2%, or even no greater than 1%. Similarly, items 30, 220, 230, 320, 330, 420, and 430 in FIGS. 3 and 5-7 can each independently be uniform, substantially uniform, or non-uniform, and the thickness of each can independently be the same or different.

Another aspect of the present disclosure is a method of making a fluid handling device. The method includes providing a structured material that includes one or more polydiorganosiloxane polyamides and attaching the structured material to a flex circuit. In some embodiments, the flex circuit can be a film-based flex circuit. The flex circuit can include a polyester substrate such as, for example, a polyethylene terephthalate substrate.

Attaching a structured material to a flex circuit can be accomplished using a wide variety of methods known in the art. The structured material can be secured to the flex circuit by applying heat, for example, as from an ultrasonic welding operation. For example, the structured material, the flex circuit, or both can be heated. The heating can be done either before or while contacting the structured material and the flex circuit. Attaching a structured material to a flex circuit can include applying pressure such that the structured material and the flex circuit are pressed together. Such pressure can be applied, for example, to the structured material. In some embodiments, a fluid tight seal is formed between the structured material and the flex circuit as a result of heating and/or applying pressure.

Methods of manufacturing fluid handling devices with numerous layers of raw materials and a number of process steps are known in the art. For example, the construction of a new layer in a fluid handling device can require a lithographic process such as photolithography in order to define channel and well features. After photolithography, a wet chemical processing step is typically employed to create channel and well features. One or more adhesives can optionally be applied to the item having channel and well features for adhering to another component. Such processing steps can be difficult and add to the complexity and cost of manufacturing the device. Methods of making devices according to the present disclosure can optionally avoid one or more potentially difficult processing steps or can optionally avoid use of one or more additional adhesives or other materials.

In one or more embodiments, methods of making a device according to the present disclosure optionally do not include applying or using an additional adhesive between the structured material and the flex circuit. Further, methods of making a device optionally do not include lithographic patterning (e.g., photolithographic patterning) of the structured material (to define, for example, channel and/or well features) or wet chemical processing (to create, for example, channel and/or well features).

Another aspect of the present disclosure is a method of making a fluid handling device. The method includes forming one or more microscopic features in a surface of a polymeric material. Such a material can include, for example, one or more polydiorganosiloxane polyamides. The method further includes attaching the microstructured surface to a flex circuit, as described above. The method can be performed with or without additional adhesive between the microstructured surface and the flex circuit.

In one or more embodiments, devices including a polydiorganosiloxane polyamide containing material can be capable of controlling or transporting a wide variety of fluids. Such fluids can be, for example, hydrophilic or hydrophobic. Such fluids can be, for example, aqueous (i.e., including water) or non-aqueous (i.e., not including water). Aqueous fluids include, but are not limited to, water and biological fluids such as blood, urine, wound exudates, food products stomached into a broth, and combinations thereof. Aqueous fluids can be, for example, neutral, acidic, or basic. Non-aqueous fluids can include, for example, a wide variety of organic fluids (such as, for example, alcohols, glycols, glycerols, polyalkylene glycols, esters, ethers, hydrocarbons, and combinations thereof), silicone fluids (such as, for example, polydimethylsiloxanes, polyphenylmethylsiloxanes, polydiphenylsiloxanes, and combinations thereof), fluorocarbon fluids, and combinations thereof.

Such devices that include a polydiorganosiloxane polyamide containing material can be fluid handling devices for use in diagnostic devices (e.g., medical diagnostic devices), testing devices (e.g., environmental testing devices such as those used, for example, in testing and/or purification of water and/or devices testing for bacteria and/or pathogens in the food industry), actuation devices (e.g., fluid driven actuation devices), and combinations thereof.

In one or more embodiments of the present disclosure, a device can further include one or more sources of potential. A wide variety of sources of potential can be used to establish a potential difference along a microstructured surface to encourage fluid movement from a first location to a second location. The potential can be sufficient to cause, or assist in causing, fluid flow through one or more channels, based in part on the fluid characteristics of a particular application. In one or more embodiments, a device having a microstructured surface does not rely solely on the properties of the microstructured surface to cause fluid movement by capillary action, for example. In some embodiments, a potential source can include a vacuum generator. Multiple potential sources can also be employed depending on the particular adaptation or application. Pressure differential can be an efficient fluid motivation potential that can be used to drive flow across the microstructured surface(s). Pressure differential can be established readily through use of pumping systems (e.g., pressure pumps and/or pressure systems such as a fan for elevated pressure) and/or vacuum systems (e.g., vacuum pumps and/or vacuum aspirators for reduced pressure). Fluid can also be caused to flow through channels by the action of a siphon where atmospheric pressure creates the potential to move fluid in the channels.

Examples of other potential sources include but are not limited to, magneto hydrodynamic drives, acoustic flow systems, centrifugal spinning, hydrostatic heads, gravity, absorbents, other fluid drive systems utilizing creation of a potential difference that causes or encourages fluid flow to at least to some degree, and combinations thereof. Additionally, applied field forces that act directly on the fluid, such as a centrifugal force or a magnetic field, and that cause fluid to move within the channels of the invention, can be considered as fluid motive potentials.

The individual flow channels of a microstructured surface can be substantially discrete. That is, fluid can move through the channels independently of fluid in adjacent channels. The channels independently accommodate the potential relative to one another to direct a fluid along or through a particular channel independent of adjacent channels. For example, fluid that enters one flow channel may not, to a significant degree, enter an adjacent channel, although there may be some diffusion between adjacent channels. It may be desired to effectively maintain the discreteness of the channels in order to effectively transport the fluid and maintain advantages that such channels provide. Not all channels, however, need be discrete for all embodiments. Some channels can be discrete while others are not. Additionally, channel "discreteness" can be a temporary phenomenon driven, for example, by fluctuating pressures.

The structured surface can be a microstructured surface that defines discrete flow channels that have a minimum aspect ratio (length/hydraulic radius) of 10:1, in some embodiments exceeding approximately 100:1, and in other embodiments at least 1000:1. At the top end, the aspect ratio could be indefinitely high but generally would be less than 1,000,000:1. In certain embodiments, the hydraulic radius of a channel is no greater than 300 micrometers. In many embodiments, it can be less than 100 micrometers, and can be less than 10 micrometers. Although smaller is generally better for many applications (and the hydraulic radius could be submicron in size), the hydraulic radius typically would not be less than 1 micrometer for many embodiments.

The structured surface can also be provided with a very low profile. Thus, active fluid transport devices are contemplated where the structured polydiorganosiloxane polyamide layer has a thickness of less than 5000 micrometers, and possibly less than 1500 micrometers. To do this, the channels can be defined by peaks that have a height of approximately 5 to 1200 micrometers and that have a peak distance of 10 to 2000 micrometers.

Microstructured surfaces in accordance with the present disclosure can provide flow systems in which the volume of the system is highly distributed. That is, the fluid volume that passes through such flow systems can be distributed over a large area. For example, channel density from 10 per lineal cm and up to 1,000 per lineal cm (measured across the channels) can provide for high fluid transport rates.

Fluid channels for use in the present invention can have a wide variety of geometries, but are typically rectangular and sometimes have depths of 50 to 3000 micron and widths of 50 to 3000 micron, or "V" channel patterns and sometimes have depths of 50 to 3000 micron and heights of 50 to 3000 micron with an included angle of generally 20 to 120 degrees and preferably 45 degrees. For example, a microstructured surface can have a nested construction wherein the master channels are 200 micron deep and repeat every 225 micron with three equally spaced channels in the base each 40 micron deep. Compound channels are also possible, such as rectangular channels that contain smaller rectangular or V channels within. (See, e.g., FIG. 2.)

A suitable microstructured surface of a polydiorganosiloxane polyamide containing material can be made using methods such as casting, extrusion, injection molding, embossing, hot stamping, and combinations thereof. In one method, a polydiorganosiloxane polyamide containing material is deformed or molded. This process is usually performed at an elevated temperature and perhaps under pressure. The material can be made to replicate or approximately replicate the surface structure of a master tool. Since this process can produce relatively small structures and is sometimes repeated many times over, the process is referred to as microreplication. Suitable processes for microreplication are described, for example, in U.S. Pat. No. 5,514,120 (Johnston et al.).

The following exemplary embodiments are provided by the present disclosure:

Embodiment 1

A device including a polydiorganosiloxane polyamide containing material having a microstructured surface.

Embodiment 2

The device of embodiment 1, wherein the microstructured surface includes at least one channel.

Embodiment 3

The device of embodiment 1 or 2, wherein the microstructured surface includes at least one well.

Embodiment 4

The device of any of embodiments 1 to 3, further including a flex circuit attached to the microstructured surface.

Embodiment 5

The device of any of embodiments 1 to 4, wherein the device is a fluid handling device.

Embodiment 6

The device of any of embodiments 1 to 5, wherein the microstructured surface forms a capillary device.

Embodiment 7

The device of any of embodiments 1 to 6, wherein the microstructured surface is hydrophilic.

Embodiment 8

A fluid handling device including: a flex circuit; and a structured material attached to the flex circuit, wherein the structured material includes one or more polydiorganosiloxane polyamides.

Embodiment 9

The fluid handling device of embodiment 8, wherein the structured material is a microstructured material.

Embodiment 10

The fluid handling device of embodiment 8 or 9, wherein the surface of the structured material that is attached to the flex circuit is a microstructured surface.

Embodiment 11

The fluid handling device of any of embodiments 8 to 10, wherein the structured material is adhered directly to at least a portion of the flex circuit.

Embodiment 12

The fluid handling device of any of embodiments 8 to 11, wherein the structured material is adhered directly to at least a portion of the flex circuit without additional adhesive.

Embodiment 13

The fluid handling device of any of embodiments 8 to 12, further including a source of potential.

Embodiment 14

A method of making a fluid handling device, the method including: providing a structured material including one or more polydiorganosiloxane polyamides; and attaching the structured material to a flex circuit.

Embodiment 15

A method of making a fluid handling device, the method including: forming a microstructured surface on a surface of a polymeric material including one or more polydiorganosiloxane polyamides; and attaching the microstructured surface to a flex circuit.

Embodiment 16

The method of embodiment 14 or 15, wherein the flex circuit is a film-based flex circuit.

Embodiment 17

A device or method according to any of claims 4 to 16, wherein the flex circuit includes a polyester substrate.

Embodiment 18

A device or method according to any of claims 4 to 17, wherein the flex circuit includes a polyethylene terephthalate substrate.

Embodiment 19

The method of any of embodiments 14 to 18, wherein attaching includes heating the structured material.

Embodiment 20

The method of any of embodiments 14 to 19, wherein attaching includes applying pressure to the structured material.

Embodiment 21

The method of any of embodiments 14 to 20 with the proviso that attaching does not include providing an additional adhesive material between the structured material and the flex circuit.

Embodiment 22

The method of any of embodiments 14 to 21 with the proviso that the method does not include photolithography.

Embodiment 23

The method of any of embodiments 14 to 22 with the proviso that the method does not include a wet chemical process.

The foregoing describes the invention in terms of embodiments foreseen by the inventor for which an enabling description was available, notwithstanding that insubstantial modifications of the invention, not presently foreseen, may nonetheless represent equivalents thereto.

EXAMPLES

These examples are merely for illustrative purposes only and are not meant to be limiting on the scope of the appended claims. All parts, percentages, ratios, and the like in the examples are by weight, unless noted otherwise. Solvents and other reagents used were obtained from Sigma-Aldrich Chemical Company; Milwaukee, Wis. unless otherwise noted.

TABLE 1

Abbreviations

| Abbreviation or Trade Designation | Description |
|---|---|
| 14K PDMS diamine | A polydimethylsiloxane diamine with an average molecular weight of about 14,000 g/mole that was prepared as described in U.S. Pat. No. 5,214,119 (Leir et al.) |
| W3 | 14,000 MW Silicone Polyoxamide |
| 5K PDMS diamine | A polydimethylsiloxane diamine with an average molecular weight of about 5,000 g/mole that was prepared as described in U.S. Pat. No. 5,214,119 (Leir et al.) |
| DEO | Diethyl Oxalate |
| ED | Ethylene Diamine |
| W1 | 5,000 MW Silicone Polyoxamide |
| Primed PET | 2 mil primed polyester film from Mitsubishi |
| GE SR545 MQ resin | A 60% solids solution of MQ silicate resin in toluene, commercially available from GE Silicones; Waterford, NY under the trade designation SR545 |
| T-10 release liner | 2 mil polyester with silicone release coating on one side from CP Films available from Solutia, Inc., Fieldale, VA. |
| substrate | Any of a wide variety of substates including, for example, polymers, metals, inorganics, membranes, paper, and combinations thereof. |
| MXDA | Meta-xylylene diamine |
| HD | Hexane diamine |
| THF | Tetrahydrofuran |
| W1-ED | 5,000 MW silicone polyoxamide elastomer polymerized with ethylene diamine |
| W1-MXDA | 5,000 MW silicone polyoxamide elastomer polymerized with meta-xylylene diamine |
| W1-HD | 5,000 MW silicone polyoxamide elastomer polymerized with hexane diamine |
| W2-ED | 5,000 MW silicone polyoxamide elastomer polymerized with ethylene diamine with 50% w/w GE SR545 MQ resin |
| W2-MXDA | 5,000 MW silicone polyoxamide elastomer polymerized with meta-xylylene diamine with 50% w/w GE SR545 MQ resin |
| W3-ED | 14,000 MW silicone polyoxamide elastomer polymerized with ethylene diamine |
| W2-HD | 5,000 MW silicone polyoxamide elastomer polymerized with hexane diamine with 50% w/w GE SR545 MQ resin |

Titration Method to Determine Equivalent Weight of Ester-Terminated Silicone Polyoxamdie.

Ten (10) grams (precisely weighed) of an ester-terminated silicone polyoxamide (e.g., the compound of Preparative Example 1, W1) was added to ajar. Approximately 50 grams THF solvent (not precisely weighed) was added. The contents were mixed using a magnetic stir bar mix until the mixture was homogeneous. The theoretical equivalent weight of the ester-terminated silicone polyoxamide was calculated and then an amount of N-hexylamine (precisely weighed) in the range of 3 to 4 times this number of equivalents was added. The reaction mixture was stirred for a minimum of 4 hours. Bromophenol blue (10-20 drops) was added and the contents were mixed until homogeneous. The mixture was titrated to a yellow endpoint with 1.0N (or 0.1N) hydrochloric acid. The number of equivalents of the ester-terminated silicone polyoxamide was equal to the number of equivalents of N-hexylamine added to the sample minus the number of equivalents of hydrochloric acid added during titration. The equivalent weight (grams/equivalent) was equal to the sample weight of the ester-terminated silicone polyoxamide divided by the number of equivalents of the ester-terminated silicone polyoxamide.

Inherent Viscosity (IV) for Polydiorganosiloxane Polyoxamide Block Copolymer.

Average inherent viscosities (IV) were measured at 30° C. using a Canon-Fenske viscometer (Model No. 50 P296) in a THF solution at 30° C. at a concentration of 0.2 grams per deciliter (g/dL). Inherent viscosities of the materials of the invention were found to be essentially independent of concentration in the range of 0.1 to 0.4 g/dL. The average inherent viscosities were averaged over 3 or more runs. Any variations for determining average inherent viscosities are set forth in specific Examples.

Preparative Example 1 (W1)

DEO (241.10 grams) was placed in a 3-liter, 3-neck resin flask equipped with a mechanical stirrer, heating mantle, nitrogen inlet tube (with stopcock), and an outlet tube. The flask was purged with nitrogen for 15 minutes and 5K PDMS diamine (a polydimethylsiloxane diamine with an average molecular weight of about 5,000 g/mole that was prepared as described in Example 2 in U.S. Pat. No. 5,214,119 (Leir et al.)) (2,028.40 grams, MW=4,918) was added slowly with stirring. After 8 hours at room temperature, the reaction flask was fitted with a distillation adaptor and receiver, the contents stirred and heated to 150° C. under vacuum (1 Torr, 133 Pa) for 4 hours, until no further distillate was able to be collected. The remaining liquid was cooled to room temperature to provide 2,573 grams of oxamido ester-terminated product W1. Gas chromatographic analysis of the clear, mobile liquid showed that no detectable level of diethyl oxalate remained. Molecular weight was determined by $^1$H NMR (MW=5,477 grams/mole) and titration (Equivalent weights of 2,573 grams/mole and 2,578 grams/mole).

Preparative Example 2 (W1-ED)

Into a 20° C. 10-gallon (37.85-Liter) stainless steel reaction vessel, 18158.4 grams of 5K ethyl oxalylamidopropyl terminated polydimethyl siloxane (titrated MW=5,477, which was prepared in a fashion similar to the description in the Preparative Example 1, with the volumes adjusted accordingly) was placed. The vessel was subjected to agitation (80 rpm) and purged with nitrogen flow and vacuum for 15 minutes. The reactor was then nitrogen pressurized to 5 pounds per square inch and heated to 90° C. over the course of 25 minutes. ED (0.44 pound) was added to the reactor. This addition was followed by 80 grams of toluene. Next the reactor was heated to a temperature of 105° C. and the pressure on the reactor was slowly vented over the course of 5 minutes. The reactor was then subjected to vacuum (approximately 20 mm Hg, 2666 Pa) for one hour to remove the ethanol and toluene. The reactor was then re-pressurized to 2 psig (13789 Pa) and the viscous molten product W1-ED was drained into a polytetrafluoroethylene-coated tray and allowed to cool.

Preparative Example 3 (W1-MXDA)

This example was prepared as in Preparative Example 2 except that 1.0 mole % of the ED was replaced with an equal number of moles of MXDA to make W1-MXDA.

Preparative Example 4 (W1-HD)

This example was prepared as in Preparative Example 2 except that 1.0 mole % of the ED was replaced with an equal number of moles of HD to give W1-HD.

Preparative Example 5 (W2-ED)

W1-ED was blended with GE SR545 MQ resin in a 50/50 weight ratio in solvent at 30% solids to make W2-ED.

Preparative Example 6 (W2-MADA)

W1-MXDA was blended with GE SR545 MQ resin in a 50/50 weight ratio in solvent at 30% solids to make W2-MXDA.

Preparative Example 7 (W2-HD)

W1-HD was blended with GE SR545 MQ resin in a 50/50 weight ratio in solvent at 30% solids to make W2-HD.

Example 1

W1-ED was dissolved in THF at 30% solids and coated onto primed PET, and oven-dried at 70° C. for 10 minutes to give a 0.001 inch (0.025 mm) thick dried coating. The sample was laminated to T-10 release liner.

Example 2

W1-MXDA was dissolved in THF at 30% solids and coated onto primed PET, and oven-dried at 70° C. for 10 minutes to give a 0.001 inch (0.025 mm) thick dried coating. The sample was laminated to T-10 release liner.

Example 3

W1-MXDA was dissolved in THF at 30% solids and coated onto primed PET, and oven-dried at 70° C. for 10 minutes to give a 0.003 inch (0.075 mm) thick dried coating. The sample was laminated to T-10 release liner.

Example 4

W1-HD was dissolved in THF at 30% solids and coated onto primed PET, and oven-dried at 70° C. for 10 minutes to give a 0.001 inch (0.025 mm) thick dried coating. The sample was laminated to T-10 release liner.

Example 5

W2-ED was coated onto primed PET, and oven-dried at 70° C. for 10 minutes to give a 0.001 inch (0.025 mm) thick dried coating. The sample was laminated to T-10 release liner.

Example 6

W2-MXDA was coated onto primed PET, and oven-dried at 70° C. for 10 minutes to give a 0.001 inch (0.025 mm) thick dried coating. The sample was laminated to T-10 release liner.

Example 7

W2-HD was coated onto primed PET, and oven-dried at 70° C. for 10 minutes to give a 0.001 inch (0.025 mm) thick dried coating. The sample was laminated to T-10 release liner.

Adhesive Test Procedure.

All samples were laminated using a roll lamination with heated, chrome plated, steel roll against an 80 durometer silicone rubber drive roll and pneumatic pressure. Lamination conditions were heat set point of 200-250° F. (93-121° C.), 27.5 pounds per square inch (190 kilopascals) of pressure, and 1 inch/minute (2.54 cm/minute) speed. Each sample was laminated in strips of approximately 2 inches (5 cm) in width then slit down to approximately 8 mm wide strips. Eight mm strips were then peeled using an Instron equipped with a German wheel/double stick tape pull system under the following parameters at 90° with a 1 kN load cell.

Table 2 summarizes the adhesion tests results. In general, adhesion of the silicone polyoxamide elastomer to the primed polyethylene terephthalate film was light to moderate with the main trend being that thicker samples, 0.003 inch (0.075 mm), provided better adhesion than 0.001 inch (0.025 mm) thick samples.

TABLE 2

Adhesion Test Results

| Example | Width (mm) | Average Load/Width at average value (5 high and low peaks) (N/mm) | Load at Machine Peak Load (N) | Maximum Load/Width (N) |
|---|---|---|---|---|
| 1 | 8.5 | 0.26 | 2.96 | 2.937 |
| 1 | 8.5 | 0.35 | 4.37 | 4.346 |
| 2 | 7 | 0.424 | 4.322 | 4.322 |
| 2 | 7 | 0.528 | 4.298 | 4.298 |
| 3 | 6 | 0.994 | 7.379 | 7.379 |
| 3 | 7 | 0.87 | 9.101 | 9.027 |
| 3 | 10 | 0.562 | 7.934 | 7.934 |
| 4 | 6 | 0.495 | 4.059 | 4.06 |
| 4 | 7 | 0.455 | 4.179 | 4.06 |
| 4 | 8 | 0.304 | 3.056 | 3.056 |

Water Traversal

TIMES. A 14,000 MW silicone polyoxamide elastomer polymerized with ED as prepared in Preparative Example 2 was embossed into an array of linear channels where each channel was approximately 1 mm wide by 1 mm in height. A single channel was cut from the array and cut to a length of 2 cm. Tap water (80 microliters) was placed in a single drop on a substrate that was located on a flat surface. The embossed channel was placed on the substrate with one end in contact with the water droplet. Table 3 lists the time it took for the water to traverse the channel versus the substrate on which the channel was placed (Table 3).

TABLE 3

Measured Water Traversal Times (seconds)

| Substrate | Time (sec) to move 2 cm |
|---|---|
| Glass microscope slide (VWR International, Cat. No. 48312-002) | <5 |
| 3M Magic tape (backing side) | No movement |
| 3M 355 tape (backing side) | No movement |
| Silicone wafer | 113 +/− 10 |
| Polystyrene (VWR International, Petri dish, Disposable, Sterile, top surface) | No movement |

Values represent an average of three trials, and +/− is one standard deviation.

The experiment of Table 3 was duplicated but this time the substrate/channel assembly was held in a vertical orientation (as opposed to the flat orientation of Table 3). Table 4 lists the time it took for the water to traverse the channel versus the substrate on which the channel was placed.

TABLE 4

Measured Water Traversal Times (seconds)

| Substrate | Time (sec) to move 2 cm |
|---|---|
| Glass microscope slide | <5 |
| 3M Scotch tape (backing side) | <5 |
| 3M 355 tape (backing side) | <5 |
| Silicone wafer | <5 |
| Polystyrene | <5 |

This data demonstrates that the embossed channel can be used as a fluid transport material. The rate of the transport for a given liquid will depend on the substrate the channel is attached to and the gravitational orientation to which the substrate is subjected.

The results of the embossing experiment showed that polydiorganosiloxane polyamide materials could be embossed by using pressure and a low amount of heat. This work lead to the construction of a larger tool that was capable of embossing an entire circuit. This mold was designed to be pressed into polydiorganosiloxane polyamide materials under high pressure and moderate heat, hence the thickness. Features on this mold included; channels 0.007 inch (0.18 mm) wide, 0.009 inch (0.23 mm) tall and 1.00 inch (25 mm) long and circular wells 0.070 inch (1.8 mm) in diameter and 0.030 inch (0.76 mm) deep with a step leading into the channel. It should be noted that the multi-level features, created easily with the process, are very difficult to produce using standard, layer built-up, processes typically used in fluid handling devices.

Initial attempts to create polydiorganosiloxane polyamide substrates thick enough to emboss with the new tool proved cumbersome using available equipment. However, embossing is likely a viable method when using proper equipment.

A casting method was used to produce sample lots that were used for evaluation. In the casting process, molten silicone polyoxamide elastomer polymerized with ED as prepared in Preparative Example 2 was simply poured over the mold, allowed to solidify, and removed. The solidified substrate removed nicely from the mold and produced clean, well formed channel and features.

Preparative Example 8

To a solution of 152.2 parts of methyl salicylate and 101.2 parts triethylamine in toluene (30%) was added dropwise with stirring a 40% solution of 91.5 parts of adipoyl chloride in toluene. An immediate precipitate of triethylamine hydrochloride formed. Stirring was continued for 1 hour after addition was complete. The mixture was filtered, and the filtrate was evaporated to dryness in a rotary evaporator to provide a white crystalline solid. The product was isolated by slurrying in hexane and filtering and dried in an oven. Only one product was observed by thin layer chromatography (TLC) and by nuclear magnetic resonance (NMR) spectroscopy, the structure of the product was consistent with the diester bis(2-carbomethoxyphenyl)adipate.

A 30% by weight solution of 526.0 parts of a 5K PDMS diamine and 11.6 parts of hexamethylene diamine in isopropyl alcohol was prepared. A 30% by weight solution in isopropyl alcohol of 82.9 parts of the diester bis(2-carbomethoxyphenyl)adipate as prepared as above was prepared and this solution was added suddenly to the first solution. The clear solution was stirred at room temperature overnight, during which time the viscosity of the solution rose significantly. The solution was cast into a glass tray, the solvent allowed to evaporate over several hours, then dried in an oven at 70° C. overnight to provide a clear, strong elastomeric film of silicone polyadipamide. The silicone polyadipamide was dissolved in a 50 wt % methyl ethyl ketone/50 wt % isopropanol blend at 10 wt % solids.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A device comprising a polydiorganosiloxane polyamide containing material having a microstructured surface, wherein the polydiorganosiloxane polyamide is a polydiorganosiloxane polyoxamide having a carbonyl group in the backbone and wherein the carbonyl group is bonded to another carbonyl group and is part of an oxalyl group.

2. The device of claim 1, wherein the microstructured surface comprises at least one channel.

3. The device of claim 1, wherein the microstructured surface comprises at least one well.

4. The device of claim 1, further comprising a flex circuit attached to the microstructured surface.

5. The device of claim 1, wherein the device is a fluid handling device.

6. The device of claim 1, wherein the microstructured surface forms a capillary device.

7. The device of claim 1, wherein the microstructured surface is hydrophilic.

8. A fluid handling device comprising:
a flex circuit; and
a structured material attached to the flex circuit, wherein the structured material comprises one or more polydiorganosiloxane polyamides, and wherein the polydiorganosiloxane polyamide is a polydiorganosiloxane polyoxamide having a carbonyl group in the backbone and wherein the carbonyl group is bonded to another carbonyl group and is part of an oxalyl group.

9. The fluid handling device of claim 8, wherein the structured material is a microstructured material.

10. The fluid handling device of claim 9, wherein the surface of the structured material that is attached to the flex circuit is a microstructured surface.

11. The fluid handling device of claim 8, wherein the structured material is adhered directly to at least a portion of the flex circuit.

12. The fluid handling device of claim 11, wherein the structured material is adhered directly to at least a portion of the flex circuit without additional adhesive.

13. The fluid handling device of claim 8, wherein the flex circuit comprises a polyester substrate.

14. The fluid handling device of claim 13, wherein the flex circuit comprises a polyethylene terephthalate substrate.

15. The fluid handling device of claim 8, further comprising a source of potential.

16. A method of making a fluid handling device, the method comprising:
providing a structured material comprising one or more polydiorganosiloxane polyamides, wherein the polydiorganosiloxane polyamide is a polydiorganosiloxane polyoxamide having a carbonyl group in the backbone and wherein the carbonyl group is bonded to another carbonyl group and is part of an oxalyl group; and
attaching the structured material to a flex circuit.

17. The method of claim 16, wherein the flex circuit comprises a film.

18. The method of claim 16, wherein the flex circuit comprises a polyester substrate.

19. The method of claim 18, wherein the flex circuit comprises a polyethylene terephthalate substrate.

20. The method of claim 16, wherein attaching comprises heating the structured material.

21. The method of claim 16, wherein attaching comprises applying pressure to the structured material.

22. The method of claim 16 wherein attaching does not comprise providing an additional adhesive material between the structured material and the flex circuit.

23. The method of claim 16 wherein the method does not comprise photolithography.

24. The method of claim 16 wherein the method does not comprise a wet chemical process.

25. A method of making a fluid handling device, the method comprising:
forming a microstructured surface on a surface of a polymeric material comprising one or more polydiorganosiloxane polyamides, wherein the polydiorganosiloxane polyamide is a polydiorganosiloxane polyoxamide having a carbonyl group in the backbone and wherein the carbonyl group is bonded to another carbonyl group and is part of an oxalyl group; and
attaching the microstructured surface to a flex circuit.

* * * * *

UNITED STATES PATENT AND TRADEMARK OFFICE
CERTIFICATE OF CORRECTION

| | |
|---|---|
| PATENT NO. | : 8,431,671 B2 |
| APPLICATION NO. | : 12/055386 |
| DATED | : April 30, 2013 |
| INVENTOR(S) | : Audrey A Sherman et al. |

It is certified that error appears in the above-identified patent and that said Letters Patent is hereby corrected as shown below:

In the Specification

Column 3
Line 66, Delete "thereof," and insert -- thereof; --, therefor.

Column 11
Line 55, Delete "thereof," and insert -- thereof; --, therefor.

Column 13
Line 40, Delete "Lubruzol" and insert -- Lubrizol --, therefor.

Column 18
Line 62, Delete "micro structures)." and insert -- microstructures). --, therefor.

Column 25
Line 46, Delete "substates" and insert -- substrates --, therefor.
Line 65, Delete "Polyoxamdie." and insert -- Polyoxamide. --, therefor.

Column 26
Line 1, Delete "ajar." and insert -- a jar. --, therefor.
Line 23, Delete "Canon" and insert -- Cannon --, therefor.

Column 27
Line 29, Delete "MADA" and insert -- MXDA --, therefor.

Signed and Sealed this
Fifteenth Day of October, 2013

Teresa Stanek Rea
*Deputy Director of the United States Patent and Trademark Office*